(12) United States Patent
Sonobe et al.

(10) Patent No.: US 8,518,447 B2
(45) Date of Patent: *Aug. 27, 2013

(54) METHOD FOR TREATING OR PREVENTING RENAL OR LIVER DISEASE

(71) Applicant: Kureha Corporation, Tokyo (JP)

(72) Inventors: Naohiro Sonobe, Fukushima (JP); Takashi Wakahoi, Ibaraki (JP); Mieko Kuwahara, Fukushima (JP)

(73) Assignee: Kureha Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/776,653

(22) Filed: Feb. 25, 2013

(65) Prior Publication Data

US 2013/0171206 A1    Jul. 4, 2013

Related U.S. Application Data

(63) Continuation of application No. 11/547,003, filed as application No. PCT/JP2005/006621 on Apr. 4, 2005, now Pat. No. 8,440,228.

(30) Foreign Application Priority Data

Apr. 2, 2004    (JP) .................................. 2004-110575

(51) Int. Cl.
*A61K 33/44*    (2006.01)
*A61K 9/14*    (2006.01)
*A61P 13/12*    (2006.01)

(52) U.S. Cl.
USPC ........... 424/489; 424/600; 424/125; 502/434; 502/9; 502/10; 502/432; 502/433; 502/445; 514/893

(58) Field of Classification Search
USPC ............... 424/600, 125; 502/434, 9, 10, 432, 502/433, 445; 514/893
See application file for complete search history.

(56) References Cited

U.S. PATENT DOCUMENTS

| 4,040,990 A | 8/1977 | Neely |
| 4,063,912 A | 12/1977 | Neely et al. |
| 4,064,042 A | 12/1977 | Kunin |
| 4,064,043 A | 12/1977 | Kollman |
| 4,474,853 A | 10/1984 | Watanabe |

(Continued)

FOREIGN PATENT DOCUMENTS

| CA | 1 139 673 | 6/1980 |
| CN | 1240220 | 6/1998 |

(Continued)

OTHER PUBLICATIONS

Kitagawa, "Preparation of Active Carbon from Phenol-Formaldehyde Resin", a JPese Journal "Nihon-Kagaku-Kaishi" (A Chemical Society of JP), No. 6, pp. 1144-1150, 1972.

(Continued)

*Primary Examiner* — Ernst Arnold
*Assistant Examiner* — Hong Yu
(74) *Attorney, Agent, or Firm* — Kilpatrick Townsend & Stockton LLP (57) ABSTRACT

The methods for treatment using an adsorbent having a high adsorbability, and capable of adsorbing a large amount of toxins during a retention period in an intestine, and of remarkably increasing an adsorption amount of compounds having a large molecular weight.

4 Claims, 2 Drawing Sheets

(56) References Cited

U.S. PATENT DOCUMENTS

| | | | |
|---|---|---|---|
| 4,681,764 A | 7/1987 | Endo et al. | |
| 4,761,284 A | 8/1988 | Nishimura | |
| 4,822,765 A | 4/1989 | Nishimura | |
| 5,554,370 A | 9/1996 | Uehara et al. | |
| 5,556,622 A | 9/1996 | Uehara et al. | |
| 5,573,761 A | 11/1996 | Ise et al. | |
| 2002/0176840 A1 | 11/2002 | Sonobe et al. | |
| 2003/0118581 A1* | 6/2003 | Sonobe et al. | 424/125 |
| 2004/0141963 A1 | 7/2004 | Umekawa et al. | |
| 2005/0152890 A1 | 7/2005 | Sonobe et al. | |

FOREIGN PATENT DOCUMENTS

| | | |
|---|---|---|
| DE | 3023848 C2 | 6/1980 |
| EP | 595715 | 5/1994 |
| EP | 0 711 561 | 5/1996 |
| EP | 1 249 241 A1 | 4/2002 |
| EP | 1407772 A1 | 4/2004 |
| EP | 1 440 692 A1 | 7/2004 |
| FR | 2 459 660 | 6/1980 |
| GB | 2 053 176 A | 6/1980 |
| GB | 2 053 176 | 2/1981 |
| JP | 54-089010 | 7/1979 |
| JP | 56-28766 | 3/1981 |
| JP | 57-136455 | 8/1982 |
| JP | 58-213613 | 12/1983 |
| JP | 59-006208 | 1/1984 |
| JP | 63-60009 | 11/1988 |
| JP | 64-056141 | 3/1989 |
| JP | 04-338107 | 11/1992 |
| JP | 6-229368 | 2/1993 |
| JP | 07-165407 | 6/1995 |
| JP | 08-040918 | 2/1996 |
| JP | 08-128766 | 5/1996 |
| JP | 08-208491 | 8/1996 |
| JP | 10-316578 | 12/1998 |
| JP | 11-001314 | 1/1999 |
| JP | 11-029485 | 2/1999 |
| JP | 11-049503 | 2/1999 |
| JP | 11-060664 | 3/1999 |
| JP | 11-116648 | 4/1999 |
| JP | 11-217278 | 8/1999 |
| JP | 11-292770 | 10/1999 |
| JP | 11-292771 | 10/1999 |
| JP | 2000-233916 | 8/2000 |
| JP | 2001-114852 | 4/2001 |
| JP | 2002-308785 | 4/2001 |
| JP | 2001-288238 A1 | 10/2001 |
| JP | 2004-244414 | 12/2003 |
| RU | 1836138 | 8/1993 |
| WO | 01/83368 A1 | 11/2001 |

OTHER PUBLICATIONS

Fukumoto, et al., "Production of Activated Carbon from Waste Phenol Resin", a JPese Journal "TANSO" (Carbon), No. 188, pp. 138-142, 1999.

Kasaoka, et al., "Preparation of Activated Fibrous Carbon from Phenolic Fabric and Its Molecular Sieving Properties", a JPese Journal "Nihon-Kagaku-Kaishi" (A Chemical Society of JP), No. 6, pp. 990-1000, 1987.

Fukuyama, et al., "Small angle X-ray Scattering from Glass-like Carbon and its Graphitization Behavior", a JPese Journal "TANSO" (Carbon), No. 182, pp. 85-90, 1998.

Shioya, et al., "Characterization of the Structure of Carbon Fibers by Wide-Angle and Small-Angle X-ray Scatterings", a JPese Journal "TANSO" (Carbon), No. 139, pp. 189-198, 1989.

Kitagawa, et al., "Steam Activation of Phenol-formaldehyde Resin", a JPese Journal "Kogyo-Kagaku-Zasshi" (Journal of Industrial Chemistry), vol. 73, No. 10, pp. 2100-2104, 1970.

Asada, et al., A JPese Text Book "X-sen Bunseki: Kiso-Bunseki-Kagaku Koza, No. 24" (X-ray Analysis: Basic Course of Analytical Chemistry), published by Kyoritsu Shuppan Co., Ltd., pp. 52-53, 1968.

A JPese Text Book "Saishin-no-Tanso-Zairyo Jikken Gijutsu: Bunseki, Kaiseki-Hen" (Latest Experimental Technique of Carbon Substance), edited by Carbon Society of JP, pp. 156-161, 2001.

"Activated carbon", a JPese Dictionary "Kagaku-jiten" (Chemical dictionary), Oct. 2, 2000, Tokyo Kagaku Dozin Co., Ltd.

"Hyperuricemia", et al., a JPese Dictionary "Nanzando's Medical Dictionary", Mar. 25, 1991, Nanzando Co., Ltd.

Experiment Report, "Influences of measuring and analyzing conditions on R values", Jul. 13, 2007, by JP EnviroChemicals Co., Ltd.

"Colloid Science IV, Experimental Methodology of Colloid Science", edited by "Nihon•Kagaku-Gakkai" (The Chemical Society of JP), Apr. 1, 1996, Tokyo Kagaku Dozin Co., Ltd.

Nishikawa, "Study on Pore Structure of Porous Carbons by Small-Angle X-ray Scattering", a JPese Journal "TANSO" (Carbon), No. 191, pp. 71-76, 2000.

No-address cover letter form for sending a brochure describing the commercial product "Maririn", etc., dated May 8, 2002, Gun Ei Chemical Industry Co., Ltd.

Tatsumoto, et al. "Activated carbon for recovering solvents", a JPese Text Book "Kassei-Tanso no Oyo-Gijutsu" (Applied Technology of Activated Carbon), pp. 2, 2000.

Gardizella, et al., "Carbon from Phenolic Resins: Carbon Yield and Volatile Components—Recent Studies", Interceram, vol. 41, Nol. 7/8, 461,462,464-467, 1992.

Otsubo, et al., "Director hemoperfusion with non-coated charcoal of high adsorption capacity derived from thermosetting resin", Trans Am Soc Artif Intern Organs, vol. 26, pp. 124-128, 1980.

Yang, et al., Preparation and Properties of Phenolic Resin-Based Activated Carbon Spheres With Controlled Pore Size Distribution. Carbon, May 2002, pp. 911-916, vol. 40, No. 6.

Sing et al., "Reporting Physisorption Data for Gas/Solid Systems with Special Reference to the Determination of Surface Area and Porosity", Pure & Applied Chemistry, vol. 57, No. 4, pp. 603-619, 1985, Great Britain.

Nichijinkaishi, "Effect of oral sorbent, AST-120, on serum concentration of indoxyl sulfate in uremic rats," *The JPese Journal of Nephrology*, vol. 32, No. 6, 1990, pp. 65-71.

Rinsho-Toseki, *The JPese Journal of Clinical Dialysis*, vol. 14, No. 4, 1998, pp. 433-438.

European Search Report mailed on Apr. 24, 2012 for European Application No. 05728869.8, filed Apr. 4, 2005; 3 pages.

Honda, et al., Prevention of Gastrointestinal Absorption of Phenobarbital by Activated Carbon Beads as an Oral Adsorbent, J. Pharmacobio-Dyn, vol. 13, Feb. 2, 1990, pp. 597-601.

"Activated carbon," a Japanese Dictionary "Kagaku-jiten" (Chemical dictionary), Oct. 2, 2000, Tokyo Kagaku Dozin Co., Ltd.

"Colloid Science IV, Experimental Methodology of Colloid Science," edited by "Nihon•Kagaku-Gakkai" (The Chemical Society of Japan), Apr. 1, 1996, Tokyo Kagaku Dozin Co., Ltd.

"Hyperuricemia," et al., A Japanese Dictionary "Nanzando's Medical Dictionary," Mar. 25, 1991, Nanzando Co., Ltd.

"Saishin-no-Tanso-Zairyo Jikken Gijutsu: Bunseki, Kaiseki-Hen," (Latest Experimental Technique of Carbon Substance), a Japanese Textbook, edited by Carbon Society of Japan, pp. 156-161, 2001.

Asada et al., "X-sen Bunseki: Kiso-Bunseki-Kagaku Koza, No. 24," (X-ray Analysis: Basic Course of Analytical Chemistry), a Japanese Textbook, published by Kyoritsu Shuppan Co., Ltd., pp. 52-53, 1968.

China Patent Office Action for 200580010366.6, dated Mar. 7, 2008, in English and Chinese.

Experiment Report, "Influences of measuring and analyzing conditions on R values," Jul. 13, 2007, by Japan EnviroChemicals Co., Ltd.

Fukumoto et al., "Production of Activated Carbon from Waste Phenol Resin," a Japanese Journal "TANSO" (Carbon), No. 188, pp. 138-142, 1999.

Fukuyama et al., "Small angle X-ray Scattering from Glass-like Carbon and its Graphitization Behavior," a Japanese Journal "TANSO" (Carbon), No. 182, pp. 85-90, 1998.

International Search Report for PCT/JP2005/006621, dated Jul. 5, 2005.

Kasaoka et al., "Preparation of Activated Fibrous Carbon from Phenolic Fabric and Its Molecular Sieving Properties," a Japanese Journal "Nihon-Kagaku-Kaishi" (A Chemical Society of Japan), No. 6, pp. 990-1000, 1987.

Kitagawa et al., "Steam Activation of Phenol-formaldehyde Resin," a Japanese Journal "Kogyo-Kagaku-Zasshi" (Journal of Industrial Chemistry), vol. 73, No. 10, pp. 2100-2104, 1970.

Kitagawa, "Preparation of Active Carbon from Phenol-Formaldehyde Resin," a Japanese Journal "Nihon-Kagaku-Kaishi" (A Chemical Society of Japan), No. 6, pp. 1144-1150, 1972.

Nichijinkaishi, "Effect of oral sorbent, AST-120, on serum concentration of indoxyl sulfate in uremic rats," The Japanese Journal of Nephrology, vol. 32, No. 6, 1990, pp. 65-71.

Nishikawa, "Study on Pore Structure of Porous Carbons by Small-Angle X-ray Scattering," a Japanese Journal "TANSO" (Carbon), No. 191, pp. 71-76, 2000.

Reau, N. et al., "Hemochromatosis," Digestive Disease Library, The Johns Hopkins Medical Institutions Gastroenterology and Hepatology Resource Center, pp. 1-2, 2007.

Rinsho-Toseki, The Japanese Journal of Clinical Dialysis, vol. 14, No. 4, 1998, pp. 433-438.

Shioya et al., "Characterization of the Structure of Carbon Fibers by Wide-Angle and Small-Angle X-ray Scatterings," a Japanese Journal "TANSO" (Carbon), No. 139, pp. 189-198, 1989.

Tatsumoto et al. "Activated carbon for recovering solvents," a Japanese Textbook "Kassei-Tanso no Oyo-Gijutsu" (Applied Technology of Activated Carbon), pp. 2, 2000.

* cited by examiner

Figure 3

METHOD FOR TREATING OR PREVENTING RENAL OR LIVER DISEASE

CROSS REFERENCE TO RELATED APPLICATIONS

The present application is a continuation application of U.S. application Ser. No. 11/547,003, filed Oct. 2, 2006, which application is a National Stage application under 35 U.S.C. 371, claiming priority to PCT/JP2005/06621, filed Apr. 4, 2005, which application claims the benefit of priority to Japanese Patent Application No. 2004-110575, filed Apr. 2, 2004, the teachings of which are incorporated herein by reference in their entirety for all purposes.

TECHNICAL FIELD

The present invention relates to an adsorbent for an oral administration comprising a spherical activated carbon having a small average particle diameter and a small bulk density. Further, the present invention relates to an agent for treating or preventing a renal or liver disease, comprising the adsorbent for an oral administration as an effective component.

The adsorbent for an oral administration, according to the present invention, exhibits a high adsorbability of indole which is a precursor of indoxyl sulfuric acid attracting attention as a harmful toxin in a body, and therefore, can adsorb many toxins within a given period of time in which toxins must be adsorbed, during a retention period from the oral administration to an excretion.

BACKGROUND ART

In patients suffering a lack of a renal function or a liver function, harmful toxic substances are accumulated or formed in bodies, such as blood, with a progress of a disorder of the organ functions, and thus an encephalopathia occurs, such as a disturbance of consciousness or uremia. Yearly, there is a growing number of such patients, and therefore, the development of an organ-substitute apparatus or medicament having a function to remove toxic substances from bodies, in place of such defective organs, has become a serious problem. A method for removing toxic substances by hemodialysis as an artificial kidney is prevalent. Nevertheless, the hemodialysis-based artificial kidney requires a special apparatus, and thus, a skilled specialist is required from a safe operation standpoint. Further, blood must be taken from a patient's body, and thus, there are disadvantages in that patients must bear high physical, mental and economic burdens. Accordingly, hemodialysis is not satisfactory.

As a means of remedying the above disadvantages, an oral adsorbent which can be orally administered and cure a disorder of renal and liver functions was developed and utilized [Patent Reference No. 1]. The adsorbent disclosed in Patent Reference No. 1 comprises a porous surface-modified spherical carbonaceous substance having particular functional groups, that is, a surface-modified spherical activated carbon, having a high safety factor and stable to a body, and having a useful selective adsorbability; that is, an excellent adsorbability of harmful substances in the presence of a bile acid in an intestine, and a low adsorbability of useful substances such as digestive enzymes in the intestine. For these reasons, the oral adsorbent is widely and clinically used for a patient suffering from a disorder of a liver or renal function, as an adsorbent having few side effects such as constipation. The above adsorbent disclosed in Patent Reference No. 1 was prepared by forming a spherical activated carbon from a pitch such as a petroleum pitch as a carbon source, and then carrying out an oxidizing treatment and a reducing treatment.

Further, an adsorbent for an oral administration providing an improvement in the above useful selective adsorbability, that is, an excellent adsorbability of harmful substances and a low adsorbability of useful substances in the intestine, is known (Patent Reference No. 2). The adsorbent for an oral administration disclosed in Patent Reference No. 2 is based on a finding that the above selective adsorbability is improved within a special range of a pore volume, that is, when a volume of pores having a pore diameter of 20 to 15000 nm is from not less than 0.04 mL/g to less than 0.10 mL/g. The adsorbent for an oral administration is very effective in treating diseases where a sufficient adsorption of toxins and a reduced adsorption of useful substances in the intestine are desired.

Further, a medical adsorbent composed of an activated carbon having a specific surface area of 500 to 2000 $m^2/g$, a pore volume of 0.2 to 1.0 mL/g, and a bulk density of 0.5 to 0.75 g/mL, and prepared by carbonizing and activating spherical phenol resin is known (Patent Reference No. 3). Patent Reference No. 3 mentions that the medical adsorbent disclosed therein is composed of the activated carbon having controlled properties of the specific surface area, the pore volume, the average pore diameter, the particle size, and the amount of oxides on the surface, and thus, can selectively adsorb ionic organic compounds while inhibiting the adsorption of polymers, such as polysaccharides or enzymes, necessary for a body.

It is known that, in a patient suffering from chronic renal failure, a concentration of indoxyl sulfuric acid in serum may be increased about 60 times higher than that in a healthy person, and that a concentration of indoxyl sulfuric acid in serum can be lowered, and thus, the progress of the chronic renal failure can be delayed by an administration of the oral adsorbent disclosed in the above Patent Reference No. 1 (Non-patent Reference Nos. 1 and 2). The mechanism whereby a concentration of indoxyl sulfuric acid is increased in a patient suffering from chronic renal failure is assumed as follows. That is, a part of tryptophan derived from proteins is metabolized to indole by *Escherichia coli* or the like in an intestinal tract. The indole is taken up, and converted by a sulfate conjugation to indoxyl sulfuric acid in a liver. The produced indoxyl sulfuric acid is excreted from a kidney of a healthy person. However, the excretory pathway is inhibited in a patient suffering from chronic renal failure, and thus, indoxyl sulfuric acid is accumulated in blood.

[Patent Reference No. 1]
Japanese Examined Patent Publication (Kokoku) No. 62-11611
[Patent Reference No. 2]
Japanese Patent No. 3522708 (Japanese Unexamined Patent Publication (Kokai) No. 2002-308785)
[Patent Reference No. 3]
Japanese Unexamined Patent Publication (Kokai) No. 2004-244414
[Non-patent Reference No. 1]
Nichijinkaishi (The Japanese journal of nephrology), vol. 32, No. 6, 1990, pp 65-71
[Non-patent Reference No. 2]
Rinsho-Toseki (The Japanese Journal of Clinical Dialysis), vol. 14, No. 4, 1998, pp 433-438

DISCLOSURE OF THE INVENTION

Problems to be Solved by the Invention

The above selective adsorbability is a very important property of the oral adsorbent composed of the spherical activated carbon. On the other hand, it is also very important to adsorb and remove as many as possible of toxins in a body, and as soon as possible. In general, the oral adsorbent has a retention period of about 3 to 5 hours in an upper portion of a small intestine. Therefore, a spherical activated carbon having a high adsorbability for a period of about 3 hours after contacting toxins, and an excellent initial adsorbability, is desirable.

As shown in Examples below, however, the oral adsorbents disclosed in Patent References No. 1 and No. 2 do not have a high adsorbability for about 3 hours after contacting toxins, and are conveyed to a lower portion of a small intestine and a large intestine, and then excreted outside of a body, while the adsorbability is not completely exhausted, but enough adsorbability is maintained.

Therefore, the inventors of the present invention engaged in intensive research to develop an oral adsorbent having a high adsorbability, that is, an oral adsorbent capable of adsorbing and removing a large amount of toxins, and having an excellent initial adsorption rate, and found that an oral adsorbent having an excellent adsorbability and an excellent initial adsorption rate can be obtained in an average particle diameter, that is, in a small average particle diameter, different from that of the conventionally known oral adsorbents disclosed in Patent References No. 1 and No. 2. Further, it is surprisingly found that a spherical activated carbon before particular functional groups are applied has the above excellent properties. The activated carbon found by the inventors can adsorb a large amount of toxins, particularly indole, for about 3 hours during the retention period in the upper portion of a small intestine, and thus, it becomes possible to reduce a dosage.

Further, the inventors of the present invention found that, even in the above range of the average particle diameter found by the inventors of the present invention, that is, in the above range of the small average particle diameter, an adsorbed amount of tryptophan or tryptamine having a molecular weight larger than that of indole is remarkably increased, in a bulk density range (i.e., a low bulk density range) different from that of the activated carbon disclosed in Patent Reference No. 3.

The present invention is based on the above findings.

Means for Solving the Problems

Accordingly, the present invention relates to an adsorbent for an oral administration, comprising a spherical activated carbon wherein an average particle diameter is 50 to 200 μm, a specific surface area determined by a BET method is 700 $m^2/g$ or more, and a bulk density is less than 0.54 g/mL.

Further, the present invention relates to an agent for treating or preventing a renal or liver disease, comprising the adsorbent for an oral administration as an effective component.

Effects of the Invention

The adsorbent for an oral administration of the present invention has a high adsorbability, and thus an excellent initial adsorbability. Therefore, the oral adsorbent of the present invention can very rapidly adsorb harmful toxins in a body during the general retention period in an upper portion of a small intestine, and is efficient as an agent for treating or preventing a renal or liver disease. Further, a dosage can be reduced in comparison with that of a conventional oral adsorbent.

Further, the adsorbent of the present invention has a small average particle diameter, and thus, an unpleasant granular feeling when taken into a mouth is eliminated or reduced, whereby the adsorbent can be easily administered. In addition, the inventors of the present invention carried out abdominal surgery of rats to which the adsorbent of the present invention was administered, and confirmed that the attachment of the adsorbent to an inner surface of the intestine was rarely observed, and in some cases, the amount of the adsorbents attached to the inner surface of the intestine became smaller than that of the conventional adsorbents having a larger average particle diameter, such as the oral adsorbent disclosed in Patent Reference No. 1. That is, the adsorbent of the present invention is at least comparable to the conventional oral adsorbents with respect to the attachment to the inner surface of the intestine.

BRIEF DESCRIPTION OF THE DRAWINGS

FIG. 1

FIG. 2

FIG. 3

BEST MODE FOR CARRYING OUT THE INVENTION

A spherical activated carbon used as the adsorbent for an oral administration according to the present invention means a non-surface-modified spherical activated carbon. The non-surface-modified spherical activated carbon as used herein means a spherical activated carbon having a total acidic-group amount of less than 0.30 meq/g. On the other hand, a surface-modified spherical activated carbon means a spherical activated carbon having a total acidic-group amount of 0.30 meq/g or more. As mentioned below, the non-surface-modified spherical activated carbon is a porous material prepared, for example, by heat-treating a carbonaceous precursor, and activating the resulting product, that is, an activated carbon without a subsequent surface-modification by oxidizing and reducing treatments, or an activated carbon prepared by a heat-treatment at a non-oxidizing atmosphere after the activating treatment as above. On the other hand, the surface-modified spherical activated carbon is a porous material prepared by heat-treating a carbonaceous precursor, activating the resulting product, and subsequently, carrying out a surface-modification by oxidizing and reducing treatments. The surface-modified spherical activated carbon can exhibit a moderate interaction with acids and bases. The total acidic-group amount of the non-surface-modified spherical activated carbon is preferably 0.25 meq/g or less, more preferably 0.20 meq/g or less.

The spherical activated carbon used as the adsorbent for an oral administration according to the present invention has a specified range of the average particle diameter and a specified range of the bulk density, as mentioned above. The average particle diameter is 50 to 200 μm, preferably 50 to 180 μm, more preferably 50 to 150 μm. The wording "average particle diameter" (Dv50) as used herein means a particle size at the particle size cumulative percentage of 50% in a particle size cumulative diagram based on a volume. The bulk density is less than 0.54 g/mL. The upper limit of the bulk density is preferably 0.50 g/mL (that is, not more than 0.50 g/mL, or less than 0.50 g/mL), more preferably 0.49 g/mL. There is no lower limit to the bulk density, but it is preferably 0.30 g/mL. The term "bulk density" ($\rho_B$) as used herein means a value obtained by dividing a dry weight, W (g), of spherical activated carbons filled in a vessel by a volume, V (mL), of the spherical activated carbons filled in the vessel, and can be calculated from the following equation:

$$\rho_B \text{ (g/mL)} = W \text{(g)}/V \text{(mL)} \qquad \text{[Formula 1]}$$

To the best of the knowledge of the inventors of the present invention, a spherical activated carbon having an average particle diameter of 50 to 200 μm is not known in the field of a spherical activated carbon used as an adsorbent for an oral administration. For example, all the average particle diameters of the porous spherical carbonaceous substance concretely prepared in Examples 1 to 5 of Patent Reference No. 2 are 350 μm. In this connection, Patent Reference No. 2 generally discloses the porous spherical carbonaceous substance having a diameter of 0.01 to 1 mm, i.e., 10 to 1000 μm (see for example, claim 1). However, the range of 0.01 to 1 mm is described as a "diameter", not as an average particle diameter. Further, as mentioned above, the adsorbents concretely disclosed in Examples 1 to 5 of Patent Reference No. 2 are only the porous spherical carbonaceous substances having an average particle diameter of 350 μm, and Patent Reference No. 2 does not disclose that a spherical activated carbon having an average particle diameter of 50 to 200 μm exhibits an increased adsorbing amount and an enhanced initial adsorbing rate. In this connection, in Comparative Examples of Patent Reference No. 2, the carbonaceous substance having an average particle diameter of 20 μm (Comparative Example 3) and the carbonaceous substance having an average particle diameter of 40 μm (Comparative Example 6) are disclosed. However, the carbonaceous substance having an average particle diameter of 20 μm (Comparative Example 3) was a product obtained by grinding the porous spherical carbonaceous substance prepared in Example 1 by a grinder, and it was not spherical. The carbonaceous substance having an average particle diameter of 40 μm (Comparative Example 6) is a powdery active charcoal for a medical use.

Further, Patent Reference No. 1 generally discloses a spherical carbonaceous substance having a diameter of 0.05 to 1 mm, 50 to 1000 μm, (see, for example, claim 1), and concretely discloses carbonaceous substances having a particle diameter of 0.05 to 1 mm, or 0.07 to 1 mm in Examples 1 to 3. However, it is apparent that the particle diameters in Patent Reference No. 1 are not average particle diameters, and it appears to be a range from the minimum particle diameter to the maximum particle diameter.

A technology for producing porous spherical carbonaceous substances having various properties described in Patent References No. 1 and No. 2 has rapidly been developed. As shown in Examples mentioned below, a production of the porous spherical carbonaceous substances having various desired properties has become easier, for example, using synthetic resin as a carbon source. For example, the average particle diameter can be relatively easily controlled. On the contrary, when a pitch is used as a carbon source, it is still not necessarily easy in technical terms to produce spherical activated carbons having, for example, an average particle diameter of 50 to 200 μm. At least, without a motivation to produce the spherical activated carbon having an average particle diameter of 50 to 200 μm, it would be unthinkable to produce the same. Therefore, at least at the time when Patent Reference No. 1 was filed, it was unthinkable to produce spherical activated carbons having an average particle diameter of 50 to 200 μm from a pitch.

As above, the spherical activated carbon used as the adsorbent for an oral administration according to the present invention is a spherical activated carbon having a specific range of an average particle diameter (50 to 200 μm). The average particle diameter in the present invention is smaller than the average particle diameter (350 μm) of the porous spherical carbonaceous substance concretely disclosed in Patent Reference No. 2. Further, the spherical activated carbon used as the adsorbent for an oral administration according to the present invention is characterized by a higher adsorbability and an excellent initial adsorbability, in comparison with the conventional spherical activated carbon. However, a decrease of the average particle diameter to such an extent does not provide a substantial increase of a specific surface area (outer surface area). The substantial improvement in the adsorbability of the spherical activated carbon used in the present invention cannot be explained only from the viewpoint of the increase of the specific surface area, i.e., the outer surface area.

Incidentally, the specific surface areas (outer surface areas) of 1 g of the spherical activated carbon having an average particle diameter of 350 μm and 1 g of the spherical activated carbon having an average particle diameter of 50 μm will be calculated. When the density of the spherical activated carbon is $\rho$ (g/m$^3$), and the particle diameter is d (m), the outer surface area (S) per 1 g of the spherical activated carbon can be calculated by the equation:

$$S = 32/3\rho d. \qquad \text{[equation 2]}$$

When the density ($\rho$) of the spherical activated carbon is $1 \times 10^6$ g/m$^3$ (1 g/cm$^3$), and the particle diameter (d) is $350 \times 10^{-6}$ m (350 μm), the outer surface area (S) is 0.03 m$^2$/g. Similarly, when the particle diameter (d) is $50 \times 10^{-6}$ m (50 μm), the outer surface area (S) is 0.21 m$^2$/g. The difference therebetween is 0.18 m$^2$/g. The specific surface area of the spherical activated carbon according to the present invention is 700 m$^2$/g, and thus, an outer surface area increase derived from the decrease of the particle diameter is less than 0.1% in the whole specific surface area.

The spherical activated carbon used as the adsorbent for an oral administration according to the present invention preferably has a narrow size distribution. For example, when a length average particle diameter of a number-based distribution is $D_1 (= \Sigma nD/\Sigma n)$, and a weight average particle diameter of a weight-based-distribution is $D_4 (= \Sigma(nD^4)/\Sigma(nD^3))$, the ratio ($D_4/D_1$) of the spherical activated carbon used as the adsorbent for an oral administration according to the present invention is preferably 3 or less, more preferably 2 or less, particularly preferably 1.5 or less. This means that the nearer the above ratio ($D_4/D_1$) is to 1, the narrower the size distribution. In the above equation, D is a representative particle diameter in a fraction of the particle diameters measured, and n is the number of particles.

The spherical activated carbons having an average particle diameter of 50 to 200 μm are disclosed in Examples of Patent Reference No. 3. However, Patent Reference No. 3 generally defines the average particle diameter as 350 μm or less, but does not disclose that particularly advantageous effects can be obtained when the average particle diameter is 200 μm or less, or that a spherical activated carbon having an average particle diameter of 50 to 200 μm exhibits an excellent initial adsorbability. As above, in Examples of Patent Reference No. 3, only the spherical activated carbons having an average particle diameter of 60 to 117 μm are produced. Further, the range of the bulk density of the spherical activated carbons concretely produced in Examples of Patent Reference No. 3 is from 0.54 to 0.61 g/mL. In addition, Patent Reference No. 3 explicitly mentions that when the bulk density (packing density) is 0.5 g/mL or less, pore diameters of the activated carbons become larger, high molecular compounds, for example, proteins (enzymes) such as trypsin or polysaccharides such as pullulan might be adsorbed, and thus a dosage becomes unfavorably larger. Therefore, Patent Reference No. 3 does not disclose a spherical activated carbon having a bulk density of less than 0.54 g/mL, or at least does not disclose a spherical activated carbon having a bulk density of 0.50 g/mL or less, or less than 0.50 g/mL.

A bulk density is a good index showing the degree of the activation, for a surface-modified spherical activated carbon or a spherical activated carbon. This means that the smaller the bulk density, the more the activation proceeds. In the process for producing the surface-modified spherical activated carbon or the spherical activated carbon, relatively small pores are formed in the initial stage of the activation with steam as mentioned below, and then, as the activation proceeds, the pore sizes are enlarged and thus, the bulk density is lowered.

The reason that the adsorbent for an oral administration according to the present invention exhibits excellent effects as mentioned above has not been elucidated at the present time, but can be presumed as follows. However, the present invention is not limited by the presumption given below:

Proteins and amino acids are taken into a person as essential nutrients. However, the taken amount greatly exceeds the amount required to grow and maintain constitutional components for a body, and as a result, the taken nitrogen compounds are degraded and eliminated from a whole body. If a liver function or a renal function is damaged, the nitrogen compounds are insufficiently metabolized and eliminated, and thus, accumulated in a body to become uremic substances. Therefore, it is preferable that the adsorbent has properties to adsorb various molecules having a broad spectrum of molecular weights from several tens to several hundred, so as to enhance the adsorbability of the oral adsorbent for adsorbing uremic substances. The adsorbent for an oral administration according to the present invention has a small particle diameter and an increased outer surface area, whereby an area where the uremic molecules are brought into contact with the adsorbent for an oral administration is increased. Further, the adsorbent for an oral administration according to the present invention has a small particle diameter and thus, the mean free path becomes shorter when the uremic substances are diffused into the particle of the oral adsorbents, whereby an adsorbing rate becomes faster. As the bulk density is low and the pore size is enlarged, relatively large molecules can be adsorbed. Accordingly, compounds having a wide spectrum of molecular weights can be adsorbed.

A carbon source for the spherical activated carbon used as the adsorbent for an oral administration of the present invention may be any carbon-containing material. The carbon-containing material which may be used is, for example, a synthetic resin or pitch. A heat-fusible resin or a heat-infusible resin can be used as the synthetic resin. The term "heat-fusible resin" as used herein means a resin from which an activated carbon cannot be produced because it is melted and decomposed as a temperature is raised, if an activation treatment is carried out before a treatment to impart infusibility. However, when the heat-fusible resin is treated to impart infusibility in advance, and then is activated, an activated carbon can be produced therefrom. On the contrary, the heat-infusible resin means a resin from which an activated carbon can be produced by the proceeding of carbonization without melting as a temperature is raised, even if a treatment to impart infusibility is not carried out in advance. The treatment to impart infusibility is, for example, an oxidation treatment carried out at 150° C. to 400° C. under an atmosphere containing oxygen, as mentioned below.

A typical example of the heat-fusible resin is a thermoplastic resin, such as a cross-linked vinyl resin. A typical example of the heat-infusible resin is a thermosetting resin, such as a phenol or furan resin. Any known thermoplastic or thermosetting resin from which a spherical shape is formed can be used. When the spherical activated carbon is produced from the cross-linked vinyl resin, the above treatment to impart infusibility is necessary. On the other hand, the above treatment to impart infusibility is not necessary when the spherical activated carbon is produced from an ion-exchange resin prepared by applying functional groups to the cross-linked vinyl resin. It is believed that the cross-linked resin is modified from the heat-fusible resin to the heat-infusible resin by the treatment used to introduce the functional groups thereto, and the functional groups introduced thereby. That is, the cross-linked vinyl resin belongs to the heat-fusible resin as used herein, whereas the ion-exchange resin belongs to the heat-infusible resin as used herein.

As a carbon source in the present invention, an ion-exchange resin, a cross-linked vinyl resin, or pitch is preferably used, and an ion-exchange resin or a cross-linked vinyl resin is more preferably used.

When the heat-infusible resin such as an ion-exchange resin is used as a carbon source for the preparation of the spherical activated carbon used as the adsorbent for an oral administration of the present invention, a method substantially the same as a conventional method for production from pitch can be used. For example, a spherical material of a heat-infusible resin is initially activated at 700 to 1000° C. in a gas stream reactive with carbon (for example, steam or carbon dioxide gas) to obtain the spherical activated carbon. The term "activated carbon" as used herein means a porous product prepared by a heat-treatment of a carbon precursor such as a spherical heat-infusible resin, and a subsequent activation, and the term "spherical activated carbon" as used herein means an activated carbon having a spherical shape and a specific surface area of 100 m$^2$/g or more. In the present invention, the spherical activated carbon having a specific surface area of 700 m$^2$/g or more, more preferably 1300 m$^2$/g or more, particularly preferably 1650 m$^2$/g or more is used. An average particle diameter of the spherical heat-infusible resin used as a starting material is preferably about 70 to 500 μm, more preferably 10 to 300 μm.

When the heat-fusible resin such as a cross-linked vinyl resin is used as a carbon source, the spherical material of a heat-fusible resin is softened by the heat-treatment and changed to an aspherical shape, or fused together by the heat-treatment. The softening can be inhibited by an oxidation at 150° C. to 400° C. in an atmosphere containing oxygen, as a treatment to impart infusibility before the activation as above.

Further, if many pyrolysis gases or the like are generated by the heat-treatment of the spherical heat-fusible resin which has been treated to impart infusibility or the spherical heat-infusible resin, pyrolysis products may be removed in advance by carrying out a pre-calcination, prior to the activation.

When pitch is used as a carbon source for the production of the spherical activated carbon used as the adsorbent for an oral administration of the present invention, the spherical activated carbon having an average particle diameter of 50 to 200 μm can be prepared by the following methods.

A dicyclic or tricyclic aromatic compound having a boiling point of 200° C. or more or a mixture thereof is added as an additive to a pitch such as a petroleum pitch or a coal pitch. The whole is heated and mixed, and then shaped to obtain a shaped pitch. The size of the shaped pitch can be controlled by a nozzle size used in an extrusion molding, or crushing conditions of the shaped pitch. The smaller the volume of the shaped pitch, the smaller the spherical pitch which may be produced, and thus, the smaller the particle diameter of the spherical activated carbon which may be produced.

Then, the shaped pitch is dispersed and granulated in hot water at 50° C. to 120° C., with stirring, to obtain a microspherical shaped pitch. The microspherical shaped pitch is cooled to obtain a spherically shaped pitch. The average particle diameter of the spherically shaped pitch is preferably 60 to 350 μm, more preferably 60 to 300 μm. Further, the additive is extracted and removed from the spherically shaped pitch by a solvent having a low solubility to the pitch but a high solubility to the additive, to thereby obtain a porous pitch. The porous pitch is oxidized with an oxidizing agent to be an infusible porous pitch. Further, the resulting heat-infusible porous pitch is treated at 800 to 1000° C. with a gas stream reactive with carbon (for example, steam or carbon dioxide gas) to obtain a spherical activated carbon.

The purpose of the addition of the aromatic compound as above is that the porous pitch is produced by extracting and removing the additive from the shaped pitch, whereby a structure control and a calcination of the carbonaceous material by oxidization in the subsequent steps is made easier. As the additive, for example, naphthalene, methylnaphthalene, phenyl-naphthalene, benzyl-naphthalene, methylanthracene, phenanthrene, or biphenyl may be used alone or in a mixture thereof. An amount of the additive added to the pitch is preferably 10 to 50 parts by weight of the aromatic compound with respect to 100 parts by weight of the pitch.

The pitch and the additive are mixed under a melted condition with heating, to achieve a homogeneous mixing. The shaping may be conducted during the melted condition, or by grinding the mixture after cooling. However, a method comprising filamentously extruding a mixed pitch under melted condition, and then, cutting the extruded product into an equally length or crushing the extruded product is preferable, because a distribution of the particle diameter can be controlled in a narrower range. The particle diameter may be controlled by the nozzle diameter used in the extrusion of the mixed pitch. A thin nozzle can be used to obtain the smaller shaped mixed pitch.

A preferable solvent used to extract and remove the additive from the mixture of the pitch and the additive may be, for example, an aliphatic hydrocarbon, such as butane, pentane, hexane, or heptane, a mixture comprising an aliphatic hydrocarbon as a main component, such as naphtha or kerosene, or an aliphatic alcohol, such as methanol, ethanol, propanol, or butanol.

The additive may be removed from the shaped mixture by extracting the additive with the solvent from the shaped mixture of the pitch and the additive, while maintaining the shape. It is assumed that, upon the extraction, through-holes of the additive are formed in the shaped product, and a shaped pitch having a uniform porosity can be obtained.

Then, the resulting shaped porous pitch is treated to impart infusibility, that is, oxidized with an oxidizing agent, preferably at 150° C. to 400° C. to obtain the shaped porous infusible pitch having a non-fusibility to heat. As the oxidizing agent, for example, oxygen gas ($O_2$), or a gas mixture prepared by diluting oxygen gas ($O_2$) with air, nitrogen or the like may be used.

When pitch is used as a carbon source for the production of the spherical activated carbon used as the adsorbent for an oral administration of the present invention, the pore volume can be controlled by controlling an amount or a kind of the aromatic compound added, or precipitation conditions in the pitch.

Further, the pore volume can be controlled by activating a metal-containing spherical carbonaceous material. For example, a spherical activated carbon wherein a volume of pores having a pore diameter of 7.5 to 15000 nm is 0.25 to 1.0 mL/g can be prepared by the following method.

The metal-containing spherical carbonaceous material can be prepared by, for example, (1) addition to the pitch, (2) impregnation of the porous pitch, (3) impregnation of the porous infusible pitch, (4) impregnation of the spherical carbon prepared by heating the porous infusible pitch, or (5) impregnation of the spherical activated carbon prepared by activation. The addition of a metallic compound or the impregnation with a metallic compound can be carried out by dissolving the metallic compound in a solvent, to prepare a metallic compound solution, adding the solution to a carbon precursor or impregnating a carbon precursor with the solution, and heating to evaporate and remove the solvent, to thereby obtain a metal-containing pitch, a metal-containing spherical porous pitch, a metal-containing spherical porous infusible pitch, or a metal-containing spherical activated carbon, or the like. When the metallic compound is added to the pitch or the spherical porous pitch is impregnated with the metallic compound, the above spherical activated carbon can be obtained by preparing the metal-containing spherical porous infusible pitch according to the above method; activating at 800° C. to 1000° C. in a gas stream having a reactivity to carbon, such as steam or carbon dioxide gas, or a gas mixture containing the above gas as a main component, to obtain a metal-containing porous spherical activated carbon, and washing with an acid to remove the metal. Further, when the spherical activated carbon is impregnated with the metallic compound, the above spherical activated carbon can be obtained by impregnating the spherical activated carbon with the metallic compound, carrying out again the activation, and washing with an acid to remove the metal.

Any metal which exhibits a catalytic effect in the steam activation can be used as the metal for preparing the metal-containing spherical carbonaceous material. The preferable metal is, for example, a transition metal, such as cobalt, iron, or nickel, a rare earth metal, such as yttrium, or a compound thereof, or a salt of the compound. The metallic compound or the salt of the compound may be, for example, an inorganic compound, such as a hydroxide, chloride, nitrate, or sulfate, an organic salt, such as acetylacetone salt or acetate, or an organic-inorganic complex salt, each containing the metallic element. The metal is introduced into carbon so that a metal atom concentration in the carbonaceous material before carrying out the activation treatment ranges preferably from 0.001 to 10% by weight, more preferably from 0.001 to 5% by weight.

The washing treatment is carried out to ensure a sufficient purity of the spherical activated carbon from a standpoint of a safe oral administration. It is necessary to remove a metal content by washing with water, or an acidic solution of hydrochloric acid, nitric acid, sulfuric acid, or hydrofluoric acid. After washing, the metal content of the spherical activated carbon is preferably 150 ppm or less, more preferably 100 ppm or less, particularly preferably 50 ppm or less.

The resulting spherical activated carbon is oxidized at 300 to 800° C., preferably 320 to 600° C., in an atmosphere containing 0.1 to 50 vol %, preferably 1 to 30 vol %, particularly preferably 3 to 20 volt of oxygen, and then reduced at 800 to 1200° C., preferably 800 to 1000° C., in an atmosphere of non-oxidative gas, to thereby obtain the surface-modified spherical activated carbon. The surface-modified spherical activated carbon as used herein means a porous material prepared by oxidizing and reducing the above spherical activated carbon.

In the present invention, however, the spherical activated carbon can be used as the adsorbent for an oral administration, without carrying out the oxidation and reduction steps for applying functional groups thereto as subsequent processes, that is, in the form of the spherical activated carbon.

It is important for the heat-infusible resin used as the starting material that a spherical product can be formed, and it is not fused or softened, and the shape is not changed, by a heat-treatment at a temperature of 500° C. or less. A heat-fusible resin can be preferably used, after being treated to impart infusibility, for example, oxidized, to thereby be converted to a state which can avoid a fusion.

A resin capable of obtaining a high carbonization yield by a heat-treatment is preferable as the heat-infusible resin used a starting material. If the carbonization yield is low, a strength of the spherical activated carbon becomes low. Further, undesirable pores are formed and a bulk density of the spherical activated carbon is lowered, and thus, a specific surface area per volume is lowered. Therefore, a volume to be orally administered is increased, and thus, a problem arises in that an oral administration becomes difficult. Accordingly, a heat-infusible resin having a higher carbonization yield is preferable. A yield by a heat-treatment at 800° C. in an atmosphere of non-oxidative gas is preferably 30% by weight or more, more preferably 35% by weight or more.

An ion-exchange resin is preferable as a heat-infusible resin used as a starting material, because an oral adsorbent having a high adsorbability of toxins to be removed can be produced. Generally, an ion-exchange resin comprises a copolymer (that is, a heat-fusible resin, such as a cross-linked vinyl resin) of divinylbenzene and styrene, acrylonitrile, acrylic acid, or methacrylic acid, and essentially has a structure wherein ion-exchange groups are bonded to a copolymer matrix having a three-dimensional network skeleton. The ion-exchange resin is generally classified, with respect to the kinds of ion-exchange groups, into a strongly acidic ion-exchange resin having sulfonic acid groups, a weakly acidic ion-exchange resin having carboxylic or sulfonic acid groups, a strongly basic ion-exchange resin having quaternary ammonium salts, and a weakly basic ion-exchange resin having primary or tertiary amines. In addition, a so-called hybrid ion-exchange resin having both acidic and basic ion-exchange groups is included as a special ion-exchange resin. In the present invention, all of the above ion-exchange resins may be used as a starting material.

The spherical activated carbon wherein a volume of pores having a pore diameter of 7.5 to 15000 nm is from 0.25 mL/g to 1.0 mL/g can be obtained by carrying out the activating treatment to the heat-infusible resin, particularly an ion-exchange resin, used as a carbon source according to the above-mentioned procedure.

A pitch may be used as a starting material. The pitch used as the starting material preferably has a high carbonization yield obtained by a heat treatment. If the carbonization yield is low, a strength of the spherical activated carbon becomes low. Further, undesirable pores are formed and a bulk density of the spherical activated carbon is lowered, and thus, a specific surface area per volume is lowered. Therefore, a volume to be orally administered is increased, and thus, a problem arises in that an oral administration becomes difficult. Accordingly, a pitch having a higher carbonization yield is preferable. A yield obtained by a heat-treatment at 800° C. in an atmosphere of non-oxidative gas is preferably 50% by weight or more, more preferably 60% by weight or more.

A cross-linked vinyl resin belonging to the heat-fusible resin is softened and melted when heated in an atmosphere of non-oxidative gas, and thus, only a carbonization yield of about 10% by weight is obtained at best. However, when the cross-linked vinyl resin is oxidized at 150° C. to 400° C. in an atmosphere containing oxygen as a treatment to impart infusibility, a spherical carbonaceous material with a high carbonization yield of 30% by weight or more can be obtained without softening or melting. A spherical activated carbon can be obtained by carrying out an activation treatment the same as that of the heat-infusible resin.

The cross-linked vinyl resin used as a starting material may be, for example, a spherical polymer prepared by an emulsion polymerization, a bulk polymerization, or a solution polymerization, preferably a spherical polymer prepared by a suspension polymerization. When the spherical cross-linked vinyl resin having a diameter of 50 μm or more is treated to uniformly impart infusibility, pores must be formed in advance in the cross-linked vinyl resin. The pores can be formed in the resin by adding porogen during the polymerization step. The surface area of the cross-linked vinyl resin required to uniformly impart infusibility thereto is preferably 10 m$^2$/g or more, more preferably 50 m$^2$/g or more.

For example, when the cross-linked vinyl resin is prepared by a suspension polymerization, an organic phase containing vinyl monomers, a cross-linking agent, porogen, and a polymerization initiator is added to an aqueous dispersion medium containing a dispersion-stabilizing agent, the whole is mixed with stirring to form many organic droplets suspended in an aqueous phase, and the monomers in the organic droplets are polymerized by heating, to thereby prepare the spherical cross-linked vinyl resin.

As the vinyl-based monomer, any vinyl-based monomer from which a spherical shape can be formed may be used. For example, an aromatic vinyl-based monomer, such as styrene, a styrene derivative wherein a hydrogen atom of a vinyl group or a phenyl group is substituted, or a compound wherein a heterocyclic or polycyclic compound is bonded to a vinyl group instead of a phenyl group can be used. An example of the aromatic vinyl-based monomer may be α- or β-methyl styrene, α- or β-ethyl styrene, methoxy styrene, phenyl styrene, or chlorostyrene, or, o-, m-, or p-methyl styrene, ethyl styrene, methoxy styrene, methylsilyl styrene, hydroxylstyrene, chloro-styrene, cyanostyrene, nitrostyrene, aminostyrene, carboxy-styrene, or sulfoxystyrene, sodium styrene sulfonate, or vinyl pyridine, vinyl thiophene, vinyl pyrrolidone, vinyl naphthalene, vinyl anthracene, or vinylbiphenyl. Further, an aliphatic vinyl-based monomer can be used. For example, there may be mentioned vinyl esters such as ethylene, propylene, isobutylene, diisobutylene, vinyl chloride, acrylate, methacrylate, or vinyl acetate; vinylketones such as vinyl methyl ketone, or vinyl ethyl ketone; vinylaldehydes, such as acrolein, or methacrolein; vinylethers, such as vinylmethylether, or vinylethylether; or vinyl nitriles, such as acrylonitrile, ethyl acrylonitrile, diphenyl acrylonitrile, chloro-acrylonitrile.

Any cross-linking agent which may be used for the cross-lining of the above vinyl-based monomer may be used. For example, there may be mentioned divinylbenzene, divinyl-pyridine, divinyltoluene, divinylnaphthalene, diallyl phthalate, ethylene glycol diacrylate, ethylene glycol dimethylate, divinylxylene, divinylethylbenzene, divinyl-sulfone, polyvinyl or polyallyl ether of glycol or glycerol, polyvinyl or polyallyl ether of pentaerythritol, polyvinyl or polyallyl ether of mono or dithio derivative of glycol, polyvinyl or polyallyl ether of resorcinol, divinyl ketone, divinyl sulfide, allyl acrylate, diallyl maleate, diallyl fumarate, diallyl succinate, diallyl carbonate, diallyl malonate, diallyl oxalate, diallyl adipate, diallyl sebacate, triallyl tricarballylate, triallyl aconitate, triallyl citrate, triallyl phosphate, N,N'-methylene diacrylamide, 1,2-di(α-methylmethylenesulfoneamido)ethylene, trivinylbenzene, trivinylnaphthalene, polyvinylanthracene, or trivinylcyclohexane. A particularly preferable cross-linking agent is polyvinyl aromatic hydrocarbon, such as divinylbenzene, glycol dimethacrylate such as ethylene glycol dimethacrylate, or polyvinyl hydrocarbon such as trivinyl cyclohexane). Divinylbenzene is most preferable, because of an excellent property of thermal decomposition.

As an appropriate porogen, there may be mentioned alkanol having 4 to 10 carbon atoms, such as, n-butanol, sec-butanol, 2-ethylhexanol, decanol, or 4-methyl 2-pentanol, alkyl ester having at least 7 carbon atoms, such as n-hexyl acetate, 2-ethylhexyl acetate, methyl oleate, dibutyl cebacate, dibutyl adipate, or dibutylcarbonate, alkyl ketone having 4 to 10 carbon atoms, such as dibutyl ketone or methyl isobutyl ketone, or alkyl carboxylic acid, such as heptanoic acid, aromatic hydrocarbon, such as toluene, xylene, or benzene, higher saturated aliphatic hydrocarbon, such as hexane, heptane, or isooctane, or cyclic aliphatic hydrocarbon, such as cyclohexane.

A polymerization initiator is not particularly limited, and an initiator usually used in this field can be used in the present invention. An oil soluble initiator which is soluble in a polymerizable monomer is preferable. As an example of the polymerization initiator, there may be mentioned a dialkyl peroxide, a diacyl peroxide, a peroxyester, a peroxydicarbonate, or an azo compound. More particularly, a dialkyl peroxide, such as methylethyl-peroxide, di-t-butyl peroxide, or dicumyl peroxide; a diacyl peroxide, such as isobutyrylperoxide, benzoylperoxide, 2,4-dichloro-benzoylperoxide, or 3,5,5-trimethylhexanoyl peroxide; a peroxyester, such as t-butylperoxypyvalate, t-hexyl-peroxypyvalate, t-butylperoxyneodecanoate, t-hexylperoxy-neodecanoate, 1-cyclohexyl 1-methylethylperoxy-neodecanoate, 1,1,3,3-tetramethylbutylperoxyneodecanoate, cumyl peroxyneodecanoate, or (α,α-bisneodecanoyl peroxy)diisopropylbenzene; a peroxydicarbonate, such as bis(4-t-butylcyclohexyl)peroxy-dicarbonate, di(n-propyl-oxy) dicarbonate, diisopropyl peroxydicarbonate, di(2-ethylethylperoxy)-dicarbonate, dimethoxybutylperoxy-dicarbonate, di(3-methyl 3-methoxybutylperoxy) dicarbonate; or an azo compound, such as 2,2'-azobisisobutylonitrile, 2,2'-azobis(4-methoxy-2,4-dimethylvaleronitrile, 2,2'-azobis(2,4-dimethylvaleronitrile), or 1,1'-azobis(1-cyclohexanecarbonitrile).

When the heat-fusible resin or the heat-infusible resin is used to prepare the spherical activated carbon according to the present invention, various properties, such as an average particle diameter, a pore volume, a particle size distribution, or a specific surface area, of the spherical activated carbon can be controlled by various methods. For example, the average particle diameter and the particle size distribution varies with the size of droplet in an aqueous phase, and the size of the droplet can be controlled by an amount of a suspending agent, the number of stirring revolutions, a shape of the stirring blade, or a monomer ratio in an aqueous phase, that is, a ratio of an amount of water and an amount of monomers. For example, the size of the droplet can be lowered by increasing an amount of a suspending agent, or increasing the number of stirring revolutions. Further, it is preferable to decrease an amount of monomers in an aqueous phase, not only because an aggregation of droplets can be controlled, but also because a heat of polymerization can be easily removed. However, it is not preferable, in view of productivity, that an amount of monomer ratio is too low, because an amount of monomers per a batch, and thus, an amount of synthetic resin produced is decreased.

When the controlled pore diameter is 10 nm or more, the pore volume and the specific surface area can be controlled mainly by an amount and a kind of porogen. When the controlled pore diameter is 10 nm or less, the pore volume and the specific surface area can be controlled by conditions of steam activation. In addition, the microtexture as the spherical activated carbon can be controlled by a kind of a resin, a kind and an amount of a cross-linking agent, conditions for imparting infusibility, and/or activating temperature, or the like.

In the spherical activated carbon used as the adsorbent for an oral administration of the present invention, a specific surface area (referred to as "SSA" hereinafter) determined by a BET method is 700 $m^2/g$ or more. When the spherical activated carbon has an SSA of less than 700 $m^2/g$, an adsorbability of toxic substances is unfavorably lowered. The SSA is preferably 1300 $m^2/g$ or more, more preferably 1650 $m^2/g$ or more. The upper limit of the SSA is not particularly limited, but the SSA is preferably 3000 $m^2/g$ or less in view of a bulk density and strength.

The pore volume of the spherical activated carbon used as the adsorbent for an oral administration of the present invention is not particularly limited. For example, a volume of pores having a pore diameter of 20 to 15000 nm is preferably 0.01 to 1 mL/g, more preferably from more than 0.04 mL/g to 1 mL/g. The volume is determined by a mercury press-injection method.

The crushing strength of the spherical activated carbon used as the adsorbent for an oral administration of the present invention is preferably 10 N/particle or more, more preferably 25 N/particle or more, particularly preferably 30 N/particle or more. There is no upper limit, but about 80 N/particle is sufficient. When the crushing strength is less than 10 N/particle, there is a high possibility that the spherical activated carbon will be unfavorably fractured into powder when handled or bitten upon an oral administration. This is undesirable because it is known that powdery activated carbon is liable to cause an interference of passing through an alimentary tract when orally administered, and it is preferable to maintain the spherical shape.

Properties of the spherical activated carbon used as the adsorbent for an oral administration of the present invention, namely, the average particle diameter, the bulk density, the specific surface area, the pore volume, the particle size distribution, and the crushing strength, are measured by the following methods.

(1) An Average Particle Diameter (Dv50)

A particle-sizes accumulating standard curve with respect to a volume basis is prepared by a laser diffraction apparatus for measuring particle size distribution [SALAD-3000S; Shimadzu Corporation]. A particle size at a particle-sizes accumulating ratio of 50% is determined as an average particle diameter (Dv50).

(2) A Bulk Density

This is measured in accordance with a method for measuring a packing density defined in JIS K 1474-5.7.2.

(3) A Specific Surface Area (Method for Calculating a Specific Surface Area by a BET Method)

An amount of gas adsorbed is measured by a specific surface area measuring apparatus (for example, ASAP2010 manufactured by MICROMERITICS) in accordance with a gas adsorbing method for the spherical activated carbon sample, and a specific surface area can be calculated by the following adsorption equation. More particularly, the spherical activated carbon is charged as a sample in a sample tube, and dried under a reduced pressure at 300° C. Thereafter, a weight of a dried sample is measured. Then, the test tube is cooled to −196° C., and nitrogen is introduced into the test tube, whereby nitrogen is adsorbed to the spherical activated carbon sample. A relation of a nitrogen partial pressure and an adsorbed amount (absorption-isotherm line) is measured.

BET plotting is carried out, given that a relative pressure of nitrogen is p, and an adsorbed amount at that time is v (cm$^3$/g STP). That is, the plotting in a range wherein p is 0.02 to 0.20 is carried out, in the field wherein a longitudinal axis is p/(v(1−p)), and an abscissa axis is p. Given that the gradient at that time is b (g/cm$^3$) and an intercept is c (g/cm$^3$), a specific surface area S (unit=m$^2$/g) can be calculated from the equation:

$$S=[MA\times(6.02\times10^{22})]/[22414\times1018\times(b+c)] \quad \text{[equation 3]}$$

wherein MA denotes a cross-sectional area of a nitrogen molecule, and is 0.162 nm$^2$.

(4) A Specific Surface Area (Method for Calculating a Specific Surface Area by a Langmuir's Equation)

An amount of gas adsorbed is measured by a specific surface area measuring apparatus (for example, ASAP2010 manufactured by MICROMERITICS) in accordance with a gas adsorbing method for the spherical activated carbon sample, and a specific surface area can be calculated by Langmuir's adsorption equation. More particularly, the spherical activated carbon is charged as a sample in a sample tube, and dried under a reduced pressure at 300° C. Thereafter, a weight of a dried sample is measured. Then, the test tube is cooled to −196° C., and nitrogen is introduced into the test tube, whereby nitrogen is adsorbed to the spherical activated carbon sample. A relation of a nitrogen partial pressure and an adsorbed amount (absorption-isotherm line) is measured.

Langmuir's plotting is carried out, given that a relative pressure of nitrogen is p, and an adsorbed amount at that time is v (cm$^3$/g STP). That is, the plotting in a range wherein p is 0.02 to 0.20 is carried out, in the field wherein a longitudinal axis is p/v, and an abscissa axis is p. Given that the gradient at that time is b (g/cm$^3$), a specific surface area S (unit=m$^2$/g) can be calculated from the equation:

$$S=[MA\times(6.02\times10^{23})]/[22414\times1018\times b] \quad \text{[equation 4]}$$

wherein MA denotes a cross-sectional area of a nitrogen molecule, and is 0.162 nm$^2$.

(6) A Pore Volume by a Mercury Injection Method

The pore volume can be measured by a mercury porosimeter (for example, AUTOPORE 9200 manufactured by MICROMERITICS). The spherical activated carbon is charged as a sample in a sample vessel, and degassed under a pressure of 2.67 Pa or less for 30 minutes. Then, mercury is introduced into the sample vessel, a pressure applied is gradually increased (maximum pressure=414 MPa) to force the mercury into the micropores in the spherical activated carbon sample. A pore volume distribution of the spherical activated carbon sample is measured from a relationship between the pressure and an amount of forced mercury, by equations as mentioned below.

Specifically, a volume of mercury inserted into the spherical activated carbon sample while a pressure is applied is increased from a pressure (0.06 MPa) corresponding to a pore diameter of 21 μm to the maximum pressure (414 MPa) corresponding to a pore diameter of 3 nm. A pore diameter can be calculated as follows. When mercury is forced into a cylindrical micropore having a diameter (D) by applying a pressure (P), a surface tension (γ) of mercury is balanced with a pressure acting on a section of the micropore, and thus, a following equation is held:

$$-\pi D\gamma \cos \theta = \pi(D/2)^2 \cdot P$$

wherein θ is a contact angle of mercury and a wall of the micropore. Therefore, a following equation:

$$D=(-4\gamma \cos \theta)/P$$

is held.

In the present specification, the relationship between the pressure (P) and the pore diameter (D) is calculated by an equation:

$$D=1.24/P$$

given that a surface tension of mercury is 484 dyne/cm, a contact angle of mercury and carbon is 130°, a unit of the pressure P is MPa, and a unit of the pore diameter D is μm. For example, the volume of pores having a pore diameter of 7.5 to 15000 nm corresponds to a volume of mercury inserted by applying a pressure from 0.083 MPa to 165 MPa. For example, the volume of pores having a pore diameter of 20 to 1000 nm corresponds to a volume of mercury inserted by applying a pressure from 1.24 MPa to 62.0 MPa.

The spherical activated carbon used as the adsorbent for an oral administration of the present invention has a very small particle size, and thus, when packed in a sample vessel, voids between sample particles become small. In the process for measuring the pore volume by the above mercury press-injection method, there is a step wherein mercury is injected into voids between the particles under pressure. In the step, the spherical activated carbon exhibits the same behavior as if it contains pores having a pore diameter of 8000 to 15000 nm. However, it can be confirmed from, for example, an observation by an electron microscope that the spherical activated carbon used as the adsorbent for an oral administration of the present invention does not contain pores having a pore diameter of 8000 to 15000 nm. Therefore, an amount of mercury injected into voids between particles under pressure is included in the expression "volume of pores having a pore diameter of 20 to 15000 nm" as used herein.

(7) Particle Size Distribution

A number-based particle distribution is measured by a laser diffraction apparatus for measuring particle size distribution [SALAD-3000S; Shimadzu Corporation] and a representative particle size D and the number n in a fraction of particles having particle size to be measured are determined. A length average particle diameter $D_1$, and a weight average particle diameter $D_4$ are calculated by the following equations:

$$D_1=\Sigma(nD)/\Sigma n \quad \text{[equation 5]}$$

$$D_4=\Sigma(nD^4)/\Sigma(nD^3) \quad \text{[equation 6]}$$

(8) Crushing Strength

A powder hardness meter [for example, simplified powder hardness meter manufactured by Tsutsui Scientific Instruments Co., Ltd.] is used to measure a power necessary to crush one particle of the spherical activated carbon sample. More particularly, one particle of the spherical activated carbon sample is held between two plates. If necessary, the particle is fixed by a two-side coated adhesive tape. A pressure is applied until the sample particle is crushed and the power necessary to crush the particle is measured.

The spherical activated carbon used as the adsorbent for an oral administration of the present invention exhibits an excellent adsorbability of exacerbation factors of liver diseases or harmful substances of renal diseases, and therefore, may be used as an adsorbent for an oral administration for treating or preventing a renal disease or a liver disease.

As the renal disease, there may be mentioned, for example, chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, or hypertension syndrome, or secondary renal diseases caused by these primary diseases, or a light renal failure before a dialysis therapy, and may be used in an improvement of a light renal failure before a dialysis therapy or a disease condition for a patient during a dialysis therapy (see "Clinical Nephrology", Asakura-shoten, Nishio Honda, Kenkichi Koiso, and Kiyoshi Kurokawa, 1990; and "Nephrology" Igaku-shoin, Teruo Omae and Sei Fujimi, ed., 1981).

As the liver disease, there may be mentioned, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, or dysfunction. Further, the porous spherical carbonaceous substance can be used in a treatment of a disease caused by toxic substances in a body, such as psychosis.

Therefore, when the adsorbent for an oral administration according to the present invention is used as an agent for treating or preventing a renal disease, it contains the spherical activated carbon as an effective component. When the adsorbent for an oral administration according to the present invention is used as an agent for a treatment of a liver or renal disease, a dosage thereof depends on the subject (human or other animal), age, individual differences, disease conditions, and so on. Therefore, in some cases, a dosage outside of the following dosage may be appropriate, but in general, the oral dosage in the case of a human is usually 1 to 20 g of the adsorbent per day, wherein the daily dosage may be divided into three to four portions. The dosage may be appropriately varied with the disease conditions. The formulation may be administered in any form, such as powders, granules, tablets, sugar-coated tablets, capsules, suspensions, sticks, divided packages, or emulsions. In the case of capsules, the usual gelatin capsules, or if necessary, enteric capsules may be used. In the case of tablets, the formulations must be broken into the original fine particles inside the body. The adsorbent may be used as a mixture with an electrolyte-controlling agent, such as an aluminum gel or Kayexalate.

The spherical activated carbon according to the present invention having an average particle diameter of 50 to 200 µm and the bulk density of less than 0.54 g/mL can be used as an agent for treating or preventing a renal or liver disease, in the form of a mixture with a conventionally known spherical activated carbon, that is, the spherical activated carbon or the surface-modified spherical activated carbon wherein the average particle diameter is outside the range of 50 to 200 µm, and/or the bulk density is 0.54 g/mL or more. Further, the spherical activated carbon according to the present invention having an average particle diameter of 50 to 200 µm and the bulk density of less than 0.54 g/mL can be used as an agent for treating or preventing a renal or liver disease, together with a conventionally known spherical activated carbon, that is, the spherical activated carbon or the surface-modified spherical activated carbon wherein the average particle diameter is outside the range of 50 to 200 µm, and/or the bulk density is 0.54 g/mL or more.

EXAMPLES

The present invention now will be further illustrated by, but is by no means limited to, the following Examples.

Example 1

Deionized water (220 g) and methyl cellulose (58 g) were charged into a 1 L separable flask. Further, 105 g of styrene, 184 g of divinyl benzene with a purity of 57% (57% divinylbenzene and 43% ethylvinyl benzene), 1.68 g of 2,2'-azobis (2,4-dimethylvaleronitrile), and 63 g of 1-butanol as a porogen were added thereto. Then, a replacement with a nitrogen gas was carried out. The two-phase system was stirred at 200 rpm, and heated to 55° C., and then allowed to stand for 20 hours. The resulting resin was filtered, and dried in a rotary evaporator. In a vacuum dryer, 1-butanol was removed from the resin by distillation, and the product was dried under a reduced pressure at 90° C. for 12 hours to thereby obtain a spherical porous synthetic resin having an average particle diameter of 180 µm. A specific surface area of the porous synthetic resin was about 90 $m^2$/g.

Figure 1:
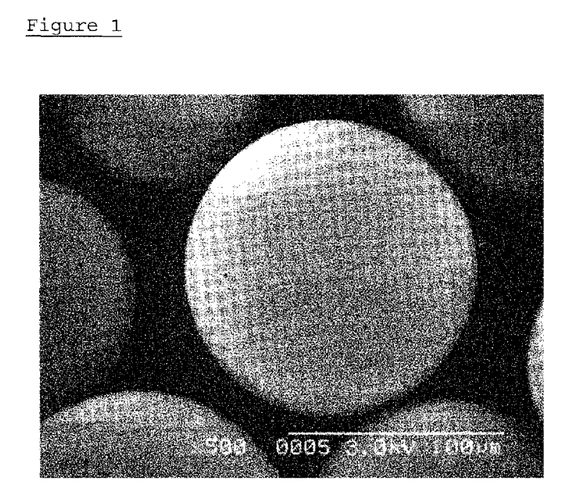
FIG. 1 is an electron microscope photograph of the spherical activated carbon according to the present invention prepared in Example 1.

The resulting spherical porous synthetic resin (100 g) was charged into a reactor having a grating, and treated to impart infusibility in a vertical tubular furnace. The infusibility-imparting treatment was carried out under the conditions that dried air (3 L/min) was upwardly passed from the lower portion of the reactor tube, the temperature was raised to 260° C. at a rate of 5° C./h, and the whole was allowed to stand at 260° C. for 4 hours to thereby obtain a spherical porous oxidized resin. The resulting spherical porous oxidized resin was heat-treated at 600° C. for 1 hour under a nitrogen atmosphere, and then activated in a fluidized bed at 820° C. for 10 hours under a nitrogen gas atmosphere containing 64.5% by volume of steam, to obtain a spherical activated carbon. FIG. 1 is an electron microscope photograph of the resulting spherical activated carbon. The properties of the resulting spherical activated carbon are listed in Table 1.

Example 2

The procedures of Example 1 were repeated except that the two-phase system was stirred at 100 rpm, instead of 200 rpm, to obtain a spherical activated carbon. The properties of the resulting spherical activated carbon are listed in Table 1.

Example 3

The procedures of Example 1 were repeated except that the two-phase system was stirred at 150 rpm, instead of 200 rpm, to obtain a spherical activated carbon. The properties of the resulting spherical activated carbon are listed in Table 1.

Example 4

The procedures of Example 1 were repeated except that the two-phase system was stirred at 300 rpm, instead of 200 rpm, to obtain a spherical activated carbon. The properties of the resulting spherical activated carbon are listed in Table 1.

Comparative Example 1

The procedures of Example 1 were repeated except that the activation was carried out for 6 hours, instead of 10 hours, to obtain a spherical activated carbon. The properties of the resulting spherical activated carbon are listed in Table 1.

Example 5

The procedures of Example 1 were repeated except that the activation was carried out for 13 hours, instead of 10 hours, to obtain a spherical activated carbon. The properties of the resulting spherical activated carbon are listed in Table 1.

Example 6

Petroleum pitch (680 g) (softening point=210° C.; quinoline insoluble contents=not more than 1% by weight; ratio of hydrogen atoms/carbon atoms=0.63) and naphthalene (320 g) were charged into an autoclave (internal volume=3 L) equipped with stirring fans, melted at 180° C., and mixed. Thereafter, the mixture was cooled to 140° C. to 160° C. and extruded through a nozzle of 0.5 mm to form string-like shaped products. Then, the string-like shaped products were broken, a section having an aperture range of 100 μm to 200 μm was obtained by passing through a sieve. The resulting broken products were added to an aqueous solution prepared by dissolving 0.23% by weight of polyvinyl alcohol (saponification value=88%), and dispersed at 95° C. for 50 minutes with stirring, to thereby obtain a spheroidized product. Then, the spheroidized product was cooled to 40° C. over 90 minutes, whereby the pitch was solidified and naphthalene crystals were precipitated, and a slurry of spherical shaped products of pitch was obtained. After most of the water was removed by filtration, the naphthalene in the spherical shaped products of pitch was extracted and removed with n-hexane at an amount by weight of about 6 times that of the spherical shaped products of pitch. The resulting porous spherical pitch was heated to 235° C. by passing a heated air in a fluidized bed, and allowed to stand at 235° C. for 1 hour, to thereby be oxidized, and a porous spherical oxidized pitch was obtained, which was non-fusible to heat. The resulting porous spherical oxidized pitch was activated in a fluidized bed at 900° C. for 174 minutes by a nitrogen gas atmosphere containing 64.5% by volume of steam to obtain a spherical activated carbon. The properties of the resulting spherical activated carbon are listed in Table 1.

Comparative Example 2

Petroleum pitch (68 kg) (softening point=210° C.; quinoline insoluble contents=not more than 1% by weight; ratio of hydrogen atoms/carbon atoms=0.63) and naphthalene (32 kg) were charged into an autoclave (internal volume=300 L) equipped with stirring fans, melted at 180° C., and mixed. Thereafter, the mixture was cooled to 140° C. to 160° C. and extruded to form string-like shaped products. Then, the string-like shaped products were broken so that a ratio of a diameter to a length became about 1 to 2. The resulting broken products were added to an aqueous solution prepared by dissolving 0.23% by weight of polyvinyl alcohol (saponification value=88%) and heating to 93° C., and dispersed with stirring to be spheroidized. Then, the whole was cooled by replacing the polyvinyl alcohol aqueous solution with water, at 20° C. for 3 hours, whereby the pitch was solidified and naphthalene crystals were precipitated, and a slurry of spherical shaped products of pitch was obtained. After most of the water was removed by filtration, the naphthalene in the spherical shaped products of pitch was extracted and removed with n-hexane at an amount by weight of about 6 times that of the spherical shaped products of pitch. The resulting porous spherical pitch was heated to 235° C. by passing a heated air in a fluidized bed, and allowed to stand at 235° C. for 1 hour, to thereby be oxidized, and a porous spherical oxidized pitch was obtained, which was non-fusible to heat. Thereafter, the resulting porous spherical oxidized pitch was activated in a fluidized bed at 820° C. for 400 minutes by a nitrogen gas atmosphere containing 64.5% by volume of steam to obtain a spherical activated carbon. The properties of the resulting spherical activated carbon are listed in Table 1.

Comparative Example 3

The spherical activated carbon obtained in Comparative Example 2 was further oxidized in the fluidized bed at 470° C. for 195 minutes under a nitrogen-oxygen atmosphere containing 18.5% by volume of oxygen, and reduced in the fluidized bed at 900° C. for 17 minutes under a nitrogen gas atmosphere to obtain a surface-modified spherical activated carbon. The properties of the resulting surface-modified spherical activated carbon are listed in Table 1.

Comparative Example 4

The procedures of Example 1 were repeated except that the two-phase system was stirred at 80 rpm, instead of 200 rpm, to obtain a spherical activated carbon. The properties of the resulting spherical activated carbon are listed in Table 1.

Comparative Example 5

The procedures of Example 1 were repeated except that the spherical activated carbon obtained by the activation treatment in Example 1 was ground for 10 seconds in a rod mill, to obtain a activated carbon. The properties of the resulting activated carbon are listed in Table 1.

Example 7

Deionized water (3003 g) and 1.4% methyl cellulose aqueous solution (530 g) were charged into a 10 L stainless steel polymerizing vessel. Further, 813 g of styrene, 1427 g of divinyl benzene with a purity of 57% (57% divinylbenzene and 43% ethylvinyl benzene), 13 g of 2,2'-azobis(2,4-dimethylvaleronitrile), and 634 g of 1-butanol as a porogen were added thereto. Then, a replacement with a nitrogen gas was carried out. The two-phase system was stirred at 220 rpm, and heated to 55° C., and then allowed to stand for 20 hours. The resulting resin was filtered, and dried in a rotary evaporator. In a vacuum dryer, 1-butanol was removed from the resin by distillation, and the product was dried under a reduced pressure at 90° C. for 12 hours to thereby obtain a spherical porous synthetic resin having an average particle diameter of 200 μm. A specific surface area of the porous synthetic resin was about 100 m²/g.

The resulting spherical porous synthetic resin (100 g) was charged into a reactor having a grating, and treated to impart infusibility in a vertical tubular furnace. The infusibility-imparting treatment was carried out under the conditions that dried air (3 L/min) was upwardly passed from the lower portion of the reactor tube, the temperature was raised to 260° C. at a rate of 5° C./h, and the whole was allowed to stand at 260° C. for 4 hours. The resulting spherical porous oxidized resin was heat-treated at 600° C. for 1 hour under a nitrogen atmosphere, and then activated in a fluidized bed at 820° C. for 13.5 hours under a nitrogen gas atmosphere containing 64.5% by volume of steam, to obtain a spherical activated carbon. The properties of the resulting spherical activated carbon are listed in Table 2.

Example 8

The procedures of Example 7 were repeated except that the activation was carried out for 11.5 hours, instead of 13.5 hours, at 820° C., to obtain a spherical activated carbon. The properties of the resulting spherical activated carbon are listed in Table 2.

Example 9

The procedures of Example 7 were repeated except that the activation was carried out for 9 hours, instead of 13.5 hours, at 820° C., to obtain a spherical activated carbon. The properties of the resulting spherical activated carbon are listed in Table 2.

Example 10

The procedures of Example 8 were repeated except that the two-phase system was stirred at 150 rpm, instead of 220 rpm, to obtain a spherical activated carbon. The properties of the resulting spherical activated carbon are listed in Table 2.

Comparative Example 6

The procedures of Example 7 were repeated except that the activation was carried out for 6 hours, instead of 13.5 hours at 820° C., to obtain a spherical activated carbon. The properties of the resulting spherical activated carbon are listed in Table 2.

Comparative Example 7

The procedures of Example 7 were repeated except that the activation was carried out for 5 hours, instead of 13.5 hours at 820° C., to obtain a spherical activated carbon. The properties of the resulting spherical activated carbon are listed in Table 2.

Comparative Example 8

The procedures of Example 8 were repeated except that the two-phase system was stirred at 75 rpm, instead of 220 rpm, to obtain a spherical activated carbon. The properties of the resulting spherical activated carbon are listed in Table 2.

Comparative Example 9

Spherical phenolic resin ("Maririn" HF500; Gun Ei Chemical Industry Co., Ltd.) was sieved through a screen to remove fine powders. Then, 150 g of the resulting spherical phenolic resin was charged into a vertical reaction quartz tube having a grating, and maintained at 700° C. for 1 hour. After allowing to stand for cooling, the whole was washed with deionazed water, and dried to obtain a spherical carbonaceous material. The resulting spherical carbonaceous material was activated at 820° C. for 6 hours in a fluidized bed at a nitrogen gas atmosphere containing 64.5% by volume of steam, to thereby obtain a spherical activated carbon. The properties of the resulting spherical activated carbon are listed in Table 2.

[Method for Evaluation of the Oral Adsorbents]
The properties shown in the following Tables 1 and 2 were measured by the following methods.
(1) Average Particle Diameter
The laser diffraction apparatus for measuring particle size distribution as mentioned above was used for the measuring.
(2) Pore Volume
The surface-modified spherical activated carbon or the spherical activated carbon prepared in Examples and Comparative Examples was measured by the mercury injection method as mentioned above.
(3) Specific Surface Area by BET or Langmuir's Method
The BET or Langmuir's method as mentioned above was used for the measuring.
(4) Bulk Density
The sample was charged into a 50 mL graduated measuring cylinder until the sample reached a scale of 50 mL. After the cylinder was tapped 50 times, a weight of the sample was divided by a volume of the sample to find a bulk density. The results are shown in Tables 1 and 2. It was confirmed that the results obtained by the above method were equal to those obtained by the method for determining a packing density in accordance with JIS K 1474-5.7.2 in the range of the significant figures shown in Tables 1 and 2.
(5) Crushing Strength
A powder hardness meter [for example, simplified powder hardness meter manufactured by Tsutsui Scientific Instruments Co., Ltd.] is used to measure a power necessary to crush one particle of the spherical activated carbon sample. More particularly, one particle of the spherical activated carbon sample is held between two plates. If necessary, the particle is fixed by a two-side coated adhesive tape. A pressure is applied until the sample particle is crushed and the power necessary to crush the particle is measured. The larger the particle size, the larger the crushing strength. Therefore, when the strength of the particle having an average particle diameter Dv50 of 200 μm or more was measured, the sample clogged on a sieve having an aperture of 425 μm was used. When the strength of the particle having an average particle diameter Dv50 of 200 μm or less was measured, the sample having a particle diameter of 75 μm to 180 μm was obtained by sieving and the crushing strength thereof was measured. The measuring procedures were carried out 20 times, and the average thereof was recorded as the crushing strength. The results are shown in Tables 1 and 2.
(6) Adsorption Test of α-Amylase
The spherical activated carbon sample or the surface-modified spherical activated carbon sample was dried, and 0.500 g of the dried sample was accurately weighed and charged into a conical flask equipped with a ground-in stopper. On the other hand, 0.100 g of α-amylase (liquefied type) was accurately weighed and dissolved by adding a phosphate buffer (pH 7.4) to prepare a stock solution having an accurate volume of 1000 mL. The stock solution in an accurate amount of 50 mL was charged to the conical flask equipped with a ground-in stopper. The flask was shaken at 37+1° C. for 3 hours. The product in the flask was filtered with suction through a 0.65 μm membrane filter. A first filtrate (about 20 mL) was discarded, and a subsequent filtrate (about 10 mL) was taken as a sample solution.
Further, the same procedures were repeated except that only a phosphate buffer (pH 7.4) was used, to obtain a filtrate as a correction solution. The sample solution and the correction solution were analyzed by an absorptiometeric analysis, using a phosphate buffer (pH 7.4) as a control. The absorbance at a wavelength of 282 nm was measured. A difference between the absorbance of the sample solution and the absorbance of the correction solution was taken as a test absorbance.

A standard curve was prepared by adding the α-amylase stock solution in an accurate amount of 0 mL, 25 mL, 50 mL, 75 mL, or 100 mL to a measuring flask, adding a phosphate buffer (pH 7.4) to 100 mL, and measuring an absorbance at a wavelength of 282 nm. From the test absorbance and the standard curve, an amount (mg/dL) of α-amylase adsorbed in the solution was calculated. The results are shown in Tables 1 and 2.

(7) Adsorption Test of Indole

An adsorption test of indole for the spherical activated carbon or the surface-modified activated carbon prepared in Examples 1 to 10 or Comparative Examples 1 to 9 was carried out, as follows.

The spherical activated carbon sample or the surface-modified spherical activated carbon sample was dried, and 0.01 g of the dried sample was accurately weighed and charged into a conical flask equipped with a ground-in stopper. 50 mL of an indole aqueous solution (indole concentration=100 mg/L) prepared by dissolving indole by adding a phosphate buffer (pH 7.4) was charged to the conical flask equipped with a ground-in stopper. The flask was shaken at 40° C. for 3 hours by a shaker. The product in the flask was filtered. The resulting filtrate was analyzed by an ultraviolet adsorption (265 nm) to measure a residual amount of indole, and calculate an amount of indole adsorbed. The results are shown in Tables 1 and 2.

(8) Change in an Adsorbed Amount of Indole with Time

In the above-mentioned test (7), "Adsorption test of indole", the spherical activated carbon sample was brought into contact with and shaken with indole for a predetermined period of time, i.e., for 3 hours. On the contrary, in the present test, the shaking time was varied and a change of an adsorption rate was measured for the spherical activated carbon prepared in Example 1, Comparative Example 2 or Comparative Example 3.

Figure 2:
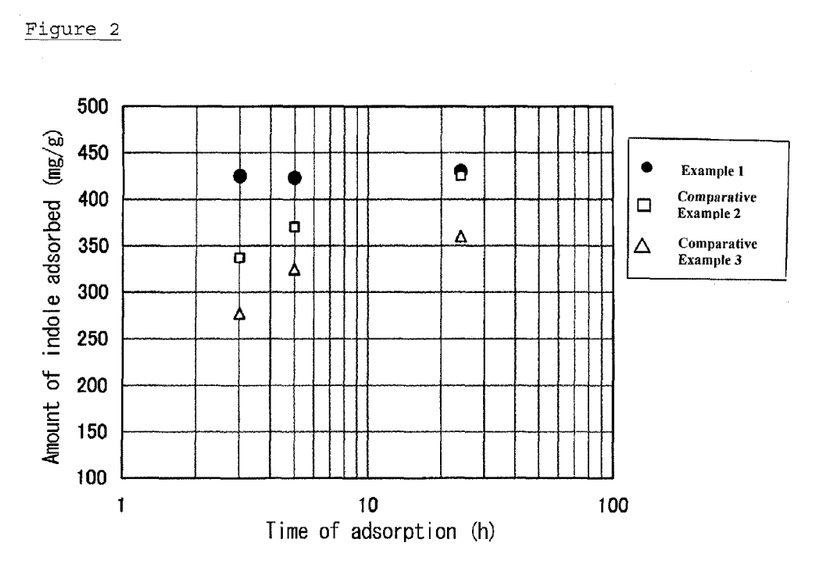
FIG. 2 is a graph showing a variation in adsorbing rates when a shaking time varies, for the spherical activated carbon prepared in Example 1, and Comparative Examples 1 and 2.

The amounts of indole adsorbed were determined according to the method mentioned in the above item (7) when the shaking time was 3 hours, 5 hours, or 24 hours. The results are shown in FIG. 2.

Figure 3:
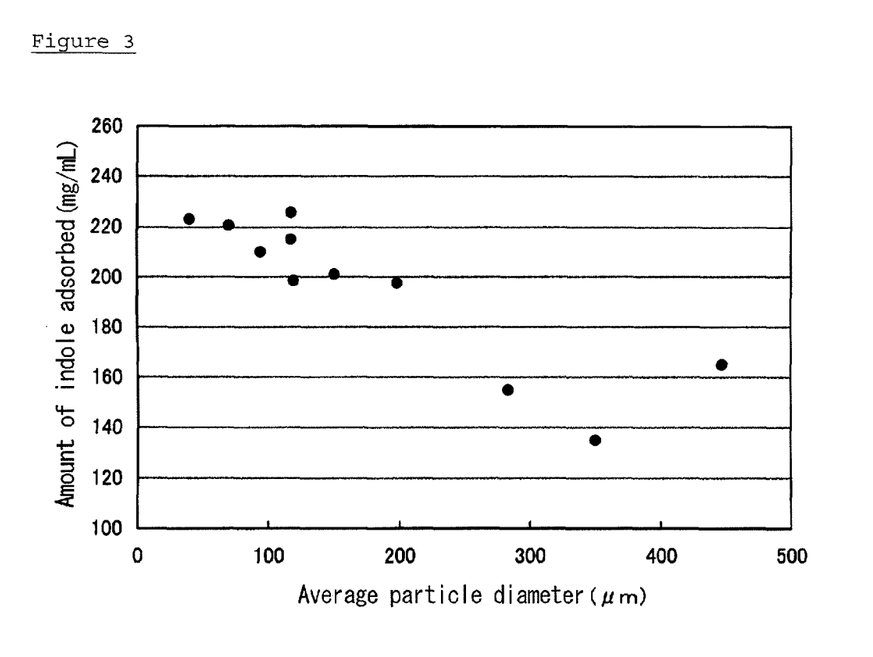
FIG. 3 is a graph showing the relationship between the average particle diameter of the spherical activated carbon and the amount of indole adsorbed by the spherical activated carbon.

(9) Relationship Between an Average Particle Diameter and an Amount of Indole Adsorbed According to the method described in the above-mentioned test (7), "Adsorption test of indole", an amount of indole adsorbed was measured for the spherical activated carbon having various average particle diameters to examine the relationship between an average particle diameter and an amount of indole adsorbed. The results are shown in FIG. 3. It was found that an excellent adsorbability of indole was observed in a range of 50 to 200 μm of an average particle diameter.

(10) Adsorption Test of Tryptophan

An adsorption test of tryptophan for the spherical activated carbon or the surface-modified spherical activated carbon prepared in Examples 4, 6 to 10 or Comparative Examples 2, 5 to 9 was carried out, as follows.

The spherical activated carbon sample or the surface-modified spherical activated carbon sample was dried, and 0.01 g of the dried sample was accurately weighed and charged into a conical flask equipped with a ground-in stopper. 50 mL of a tryptophan aqueous solution (tryptophan concentration=100 mg/L) prepared by dissolving tryptophan by adding a phosphate buffer (pH 7.4) was charged to the conical flask equipped with a ground-in stopper. The flask was shaken at 40° C. for 3 hours by a shaker. The product in the flask was filtered. The resulting filtrate was analyzed by an ultraviolet adsorption (280 nm) to calculate an amount of tryptophan adsorbed. The results are shown in Table 2.

TABLE 1

| | | Average particle diameter | | | | Specific surface area | | | Volume of pores with pore |
|---|---|---|---|---|---|---|---|---|---|
| | | Dv50 (μm) | Length $D_1$ (μm) | Weight $D_4$ (μm) | $D_4/D_1$ | Langmuir method ($m^2/g$) | BET method ($m^2/g$) | Bulk density (g/mL) | diameter of 20-15000 nm (mL/g) |
| Example 1 | Cross-linked vinyl resin | 117 | 118 | 133 | 1.12 | 2407 | 1906 | 0.50 | 0.06 |
| Example 2 | Cross-linked vinyl resin | 198 | 168 | 196 | 1.16 | 2451 | 1978 | 0.50 | 0.05 |
| Example 3 | Cross-linked vinyl resin | 150 | 142 | 156 | 1.09 | 2380 | 1921 | 0.50 | 0.06 |
| Example 4 | Cross-linked vinyl resin | 70 | 67 | 74 | 1.11 | 2422 | 1955 | 0.50 | 0.11 |
| Example 5 | Cross-linked vinyl resin | 117 | 128 | 132 | 1.03 | 2715 | 2210 | 0.47 | 0.08 |
| Example 6 | Pitch | 94 | 88 | 109 | 1.23 | 2252 | 1853 | 0.50 | 0.15 |
| Comparative Example 1 | Cross-linked vinyl resin | 119 | 119 | 135 | 1.14 | 1443 | 1177 | 0.63 | 0.03 |
| Comparative Example 2 | Pitch | 447 | 473 | 507 | 1.07 | 2236 | 1801 | 0.50 | 0.08 |
| Comparative Example 3 | Pitch | 350 | 374 | 398 | 1.06 | 2205 | 1537 | 0.50 | 0.06 |
| Comparative Example 4 | Cross-linked vinyl resin | 283 | 288 | 326 | 1.13 | 2218 | 1525 | 0.50 | 0.03 |
| Comparative Example 5 | Cross-linked vinyl resin | 40 | 13 | 49 | 3.8 | 2320 | 1541 | 0.50 | 0.41 |

TABLE 1-continued

|  |  | Acidic points (meq/g) | Crushing strength (N/particle) | Amount of indole adsorbed (mg/g) | Amount of indole adsorbed (mg/mL) | Amount of tryptophan adsorbed (mg/g) | Adsorption amount of α-amylase (residual amount after adsorption) (mg/dL) |
|---|---|---|---|---|---|---|---|
| Example 1 | Cross-linked vinyl resin | 0.18 | >40 | 430 | 215 |  | 2.04 (7.96) |
| Example 2 | Cross-linked vinyl resin | 0.16 | >40 | 395 | 198 |  | 1.87 (8.13) |
| Example 3 | Cross-linked vinyl resin | 0.18 | >40 | 402 | 201 |  | 1.80 (8.20) |
| Example 4 | Cross-linked vinyl resin | 0.20 | >40 | 441 | 221 | 355 | 2.20 (7.80) |
| Example 5 | Cross-linked vinyl resin | 0.23 | >40 | 480 | 226 |  | 2.28 (7.72) |
| Example 6 | Pitch | 0.21 | 2.3 | 420 | 210 | 281 | 3.42 (6.58) |
| Comparative Example 1 | Cross-linked vinyl resin | 0.19 | >40 | 315 | 198 |  | 1.79 (8.21) |
| Comparative Example 2 | Pitch | 0.19 | 2.0 | 330 | 165 | 151 | 2.32 (7.68) |
| Comparative Example 3 | Pitch | 0.67 | 2.0 | 270 | 135 |  | 2.81 (7.19) |
| Comparative Example 4 | Cross-linked vinyl resin | 0.17 | >40 | 310 | 155 |  | 1.49 (8.51) |
| Comparative Example 5 | Cross-linked vinyl resin | 0.20 | unmeasurable | 445 | 223 | 375 | 4.88 (5.12) |

TABLE 2

|  | Starting material | Average particle diameter Dv50 (μm) | Specific surface area Langmuir method (m²/g) | Specific surface area BET method (m²/g) | Bulk density (g/mL) | Volume of pores with pore diameter of 20-1000 nm (mL/g) | Volume of pores with pore diameter of 20-15000 nm (mL/g) | Acidic points (meq/g) | Crushing strength (N/particle) | Amount of indole adsorbed (mg/g) | Amount of tryptophan adsorbed (mg/g) | Adsorption amount of α-amylase (mg/g) |
|---|---|---|---|---|---|---|---|---|---|---|---|---|
| Example 7 | Cross-linked vinyl resin | 101 | 2760 | 2250 | 0.47 | 0.04 | 0.07 | 0.18 | >40 | 390 | 321 | 1.9 |
| Example 8 | Cross-linked vinyl resin | 103 | 2520 | 2050 | 0.49 | 0.03 | 0.06 | 0.18 | >40 | 378 | 318 | 1.7 |
| Example 9 | Cross-linked vinyl resin | 103 | 2070 | 1680 | 0.53 | 0.03 | 0.06 | 0.17 | >40 | 365 | 307 | 1.6 |
| Example 10 | Cross-linked vinyl resin | 150 | 2530 | 2030 | 0.49 | 0.03 | 0.05 | 0.17 | >40 | 323 | 253 | 1.6 |
| Comparative Example 6 | Cross-linked vinyl resin | 105 | 1440 | 1180 | 0.60 | 0.02 | 0.03 | 0.17 | >40 | 347 | 179 | 1.5 |
| Comparative Example 7 | Cross-linked vinyl resin | 105 | 1350 | 1080 | 0.62 | 0.01 | 0.03 | 0.16 | >40 | 343 | 75 | 1.5 |
| Comparative Example 8 | Cross-linked vinyl resin | 345 | 2510 | 2030 | 0.49 | 0.04 | 0.02 | 0.19 | >40 | 261 | 165 | 1.3 |
| Comparative Example 9 | Phenol resin | 330 | 1650 | 1330 | 0.60 | 0.01 | 0.02 | 0.31 | 22 | 210 | 69 | 1.3 |

Industrial Applicability

The adsorbent for an oral administration according to the present invention can be used as an adsorbent for an oral administration for treating or preventing a renal disease, or an adsorbent for treating or preventing a liver disease.

As the renal disease, there may be mentioned, for example, chronic renal failure, acute renal failure, chronic pyelonephritis, acute pyelonephritis, chronic nephritis, acute nephritic syndrome, acute progressive nephritic syndrome, chronic nephritic syndrome, nephrotic syndrome, nephrosclerosis, interstitial nephritis, tubulopathy, lipoid nephrosis, diabetic nephropathy, renovascular hypertension, or hypertension syndrome, or secondary renal diseases caused by these primary diseases, or a light renal failure before a dialysis therapy, and may be used in an improvement of a light renal failure before a dialysis therapy or a disease condition for a patient during dialysis therapy (see "Clinical Nephrology", Asakura-shoten, Nishio Honda, Kenkichi Koiso, and Kiyoshi Kurokawa, 1990; and "Nephrology" Igaku-shoin, Teruo Omae and Sei Fujimi, ed., 1981).

As the liver disease, there may be mentioned, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, primary biliary cirrhosis, tremor, encephalopathia, dysbolism, or dysfunction. Further, the porous spherical carbonaceous substance can be used in a treatment of a disease caused by toxic substances in a body, such as psychosis.

Although the present invention has been described with reference to specific embodiments, various changes and modifications obvious to those skilled in the art are possible without departing from the scope of the appended claims.

The invention claimed is:

1. A method for treating a renal disease, the method comprising:
orally administering an adsorbent comprising a non-surface modified spherical activated carbon wherein an average particle diameter is 50 to 200 μm, and a specific surface area determined by a BET method is 700 m$^2$/g or more, further wherein said non-surface modified spherical activated carbon has a total acidic-group amount of less than 0.30 meg/g, to treat the renal disease.

2. A method for treating a liver disease, the method comprising:
orally administering an adsorbent comprising a non-surface modified spherical activated carbon wherein an average particle diameter is 50 to 200 μm, and a specific surface area determined by a BET method is 700 m$^2$/g or more, further wherein said non-surface modified spherical activated carbon has a total acidic-group amount of less than 0.30 meg/g, to treat the liver disease.

3. A method for treating a renal disease, the method comprising:
orally administering a non-surface modified spherical activated carbon wherein an average particle diameter is 50 to 200 μm, a specific surface area determined by a BET method is 700 m$^2$/g or more, and a bulk density is less than 0.54 g/mL, and further wherein said non-surface modified spherical activated carbon has a total acidic-group amount of less than 0.30 meq/g, to treat the renal disease.

4. A method for treating a liver disease, the method comprising:
orally administering a non-surface modified spherical activated carbon wherein an average particle diameter is 50 to 200 μm, a specific surface area determined by a BET method is 700 m$^2$/g or more, and a bulk density is less than 0.54 g/mL, and further wherein said non-surface modified spherical activated carbon has a total acidic-group amount of less than 0.30 meq/g, to treat the liver disease.

* * * * *